United States Patent [19]

Van Groningen

[11] Patent Number: 5,709,217
[45] Date of Patent: Jan. 20, 1998

[54] DEVICE FOR MEASURING THE RESPIRATION OF A PERSON

[75] Inventor: Johannis Van Groningen, Achthuizen, Netherlands

[73] Assignee: B.V. Optische Industrie De Oude Delft, Delft, Netherlands

[21] Appl. No.: 967,717

[22] Filed: Oct. 28, 1992

[51] Int. Cl.$^6$ .................................................. A61B 5/08
[52] U.S. Cl. ............................................................ 128/721
[58] Field of Search .................................... 128/721, 782, 128/720; 340/347; 328/DIG. 15

[56] References Cited

U.S. PATENT DOCUMENTS

| | | | |
|---|---|---|---|
| 3,097,639 | 7/1963 | Streimer | 128/721 |
| 3,782,368 | 1/1974 | Reibold | 128/721 |
| 3,930,252 | 12/1975 | Storar | 340/347 NT |
| 4,989,612 | 2/1991 | Fore | 128/721 |
| 5,015,251 | 5/1991 | Cherveini | 128/DIG. 15 |
| 5,107,855 | 4/1992 | Harrington et al. | 128/721 |

FOREIGN PATENT DOCUMENTS 2107939  8/1973  Germany ................... 128/721

*Primary Examiner*—Richard J. Apely
*Assistant Examiner*—John Mulcahy
*Attorney, Agent, or Firm*—Louis E. Marn

[57] ABSTRACT

There is disclosed a device for measuring the respiration of a person and is provided with a strap which can be applied to fit around the upper part of the body of the person and includes a detector for measuring the variation and the circumference of the upper body caused by respiration for generating a measurement signal corresponding to the variation measured by the detector for controlling a display device.

7 Claims, 2 Drawing Sheets

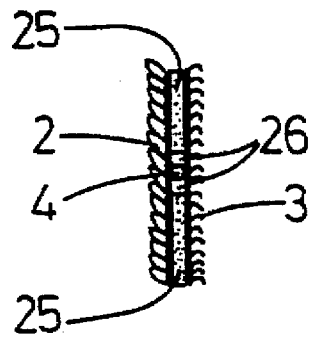
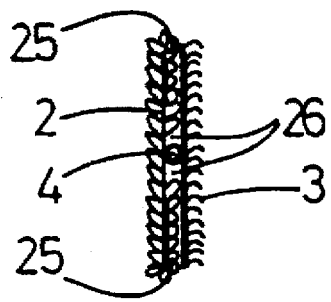
fig.6    fig.7
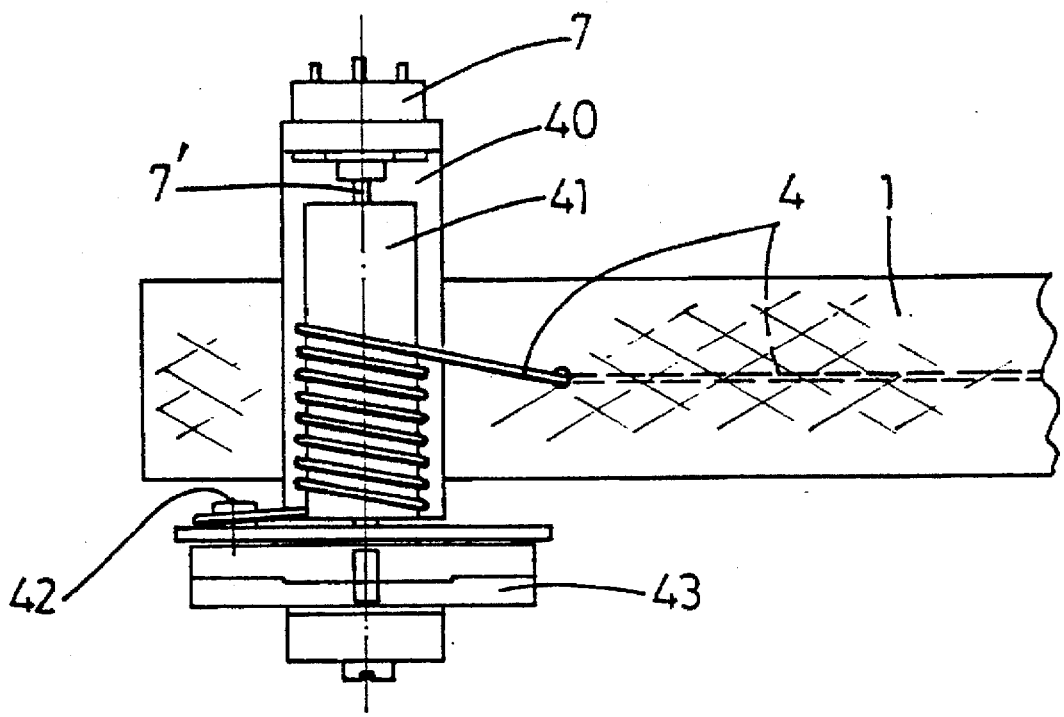
fig.4

DEVICE FOR MEASURING THE RESPIRATION OF A PERSON

The invention relates to an device for measuring the respiration of a person, provided with a strap, which can be applied so that it fits around the upper body of the person, and a detector for measuring the variation in the circumference of the upper body caused by respiration, which detector supplies a measurement signal corresponding to this variation to a processing circuit, which controls a display device for displaying this variation.

A device of this type is disclosed, for example, in U.S. Pat. No. 4,595,196. In this known device, the strap consists of non-stretchable material and the strap is constructed in two parts, which on the one hand are detachably connected to one another in order to fit the strap around the upper body and, on the other hand, are connected to the housing of the processing circuit. In this arrangement, one part of the strap is rigidly connected to said housing, while the other part of the strap is fixed to a spring element, so that this part of the strap is movable relative to the housing. The magnitude of this movement corresponds to the variation in the circumference of the upper body and is detected in a suitable manner. This known device in the first place has the disadvantage that the strap must be able to move relative to the body, as a result of which the resistance which the user encounters on breathing is dependent on various conditions, such as the clothing. Moreover, this known device has the disadvantage that the strap always has to be fitted around the upper body under a predetermined pre-tension in order to set the detector to the correct starting position.

The object of the invention is to provide an device of the type mentioned in the preamble with which device said disadvantages are overcome in a simple manner.

To this end, the device according to the invention is characterised in that the strap is made of an elastic material and can be fitted around the upper body under a desired pre-tension and in that the detector comprises an elongated element of non-stretchable material, preferably a cord, which at least virtually extends over the entire length of the strap and is supported by the strap, one end of the cord being rigidly coupled to the strap and the other end actuating a transformer which transforms the movement of the element relative to the strap into the measurement signal, which is supplied to the processing circuit.

In the case of the device according to the invention, the strap and the detector are constructed as components which function entirely separately from one another, the strap acting only as support for the detector. Consequently, the strap can be fitted around the upper body of the user under any desired pre-tension, so that this pretension can be chosen in a suitable manner for training respiration. The detector of the device according to the invention, consisting of the elongated element and the transformer, functions independently of the strap and supplies a measurement signal which corresponds to the movement of the elongated element relative to the strap, that is to say the variation in the circumference of the upper body.

According to an advantageous embodiment of the invention, the processing circuit comprises adjustment means which can be operated manually and which, on operation, set the display device to zero at the current value of the measurement signal from the detector. By this means it is achieved that the display device can be set to zero in a particularly simple manner when the user has breathed out fully after fitting of the strap.

In order to make the device suitable for diverse persons, it is preferably, according to the invention, that the processing circuit comprises an adjustment device which can be operated manually and with which the relationship between the variation in the measurement signal and the display range of the display device can be adjusted.

The invention is illustrated in more detail below with reference to the drawing, in which an exemplary embodiment is shown schematically.

FIG. 4 shows the transformer, which is designed as a potentiometer, in more detail.

FIG. 6 is a cross-section like in FIG. 2 of another embodiment of the strap of the device according to the invention.

FIG. 7 is a cross-section like in FIG. 2 of still another embodiment of the strap of the device according to the invention.

Figures 1, 2:
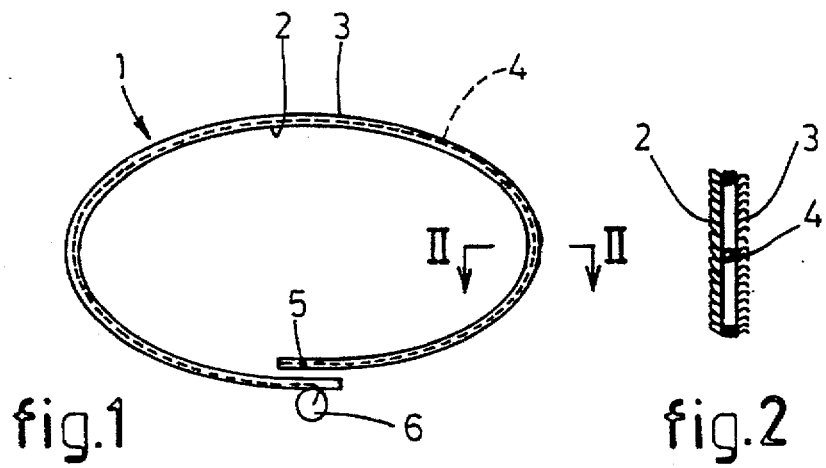
FIG. 1 is a highly schematic representation of a top view of the strap with detector of an embodiment of the device according to the invention.
FIG. 2 is a cross-section along the line II—II from FIG. 1.

FIG. 1 shows a top view of a strap 1, which can be applied so that it fits around the upper body of a person for measuring the variation in the circumference of the upper body. As indicated schematically in FIG. 2, in the embodiment shown, the strap 1 is made of an elastic strip of looped strap 2 and an elastic strip of hooked strap 3, which strips are connected to one another at the longitudinal edges, so that a hollow is obtained in which a cord 4 is fitted, which cord consists of nonstretchable material. This cord 4 is rigidly connected to the strap 1 at the end 5 of the strap 1. The other end of the cord 4 is connected to a transformer 6, which is indicated schematically and which transforms the movement of the cord 4 relative to the band 1, which movement corresponds to the variation in the circumference of the upper body, into a measurement signal corresponding thereto.

The transformer 6 is detachably coupled, in a manner which is not shown in more detail, to a processing circuit which controls a display device for displaying the variation in the circumference of the upper body of the user. Two possible embodiments of this processing circuit are indicated highly schematically in FIGS. 3 and 5.

Figure 3:
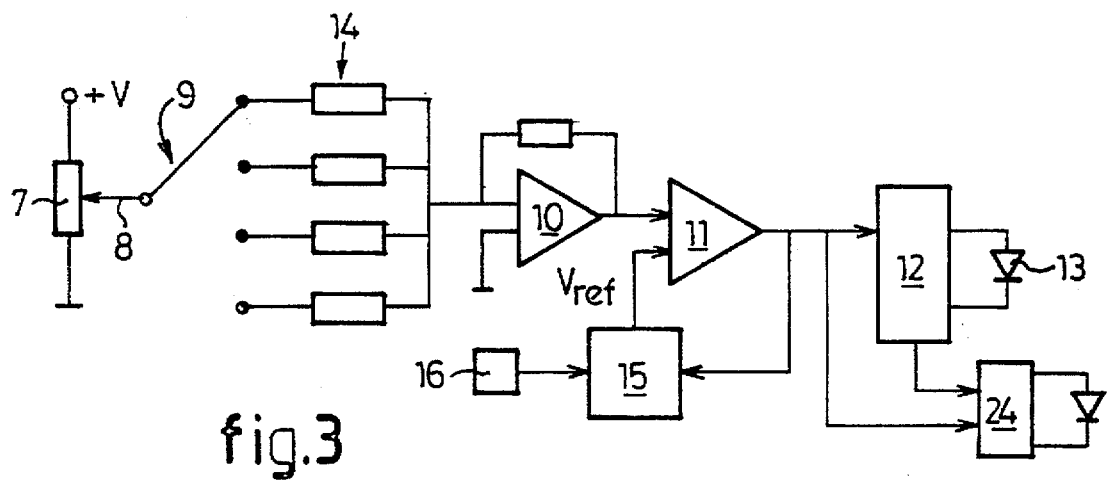
FIG. 3 is an example of a processing circuit with display device of the device according to the invention.

In the variant according to FIG. 3, the transformer comprises a potentiometer 7, the slide 8 of which is actuated by the cord 4.

The potentiometer 7 is shown in more detail in FIG. 4 and is mounted on a bracket 40, which is fixed to the end of the strap 1. The cord 4 is wound around a drum 41 and the end of the cord is clamped at 42. The drum 41 is connected to the control shaft 7' of the potentiometer 7. When a tensile force is exerted on the cord 4 by the user of the device described breathing in, the control shaft of the potentiometer is turned and a signal corresponding to the rotation can be taken from the slide 8. A spring 43, which is shown schematically, rotates the drum 41 back again during breathing out.

In a practical embodiment, the potentiometer 7, with the components 40–43, is, of course, mounted in a closed housing. The potentiometer 7 is connected between a positive power supply and earth. The slide 8 of the potentiometer 7 is connected, in the manner shown, via a multiposition switch 9 to a buffer amplifier 10, the output of which is connected to one input of a comparator 11. The other input of the comparator 11 receives an adjustable reference voltage $V_{ref}$. The comparator 11 supplies a signal which is proportional to the output signal from the buffer amplifier 10 as soon as said output signal exceeds the reference voltage $V_{ref}$. The output of the comparator is connected to a control stage 12, which, for example, controls a so-called LED bar, which is indicated schematically by a LED 13.

The multiposition switch 9, together with the resistances 14 of various values connected thereto, provides the possibility for adjusting the ratio between the measurement signal from the potentiometer 7 and the display range of the LED bar 13. By this means the sensitivity of the device described can be adjusted depending on the user concerned and depending on the degree to which this user has been trained in the desired respiration.

The circuit shown in FIG. 3 comprises a zero adjustment unit 15 with a pushbutton 16, which can be operated by hand, which zero adjustment unit 15, on operation of the button 16, adjusts the LED bar 13 to zero irrespective of the measurement signal supplied at that instant by the potentiometer 7, by adjusting the reference voltage $V_{ref}$ until the output from the comparator 11 is zero. By this means it is possible to make a fixed connection between the cord 4 and the detector 6. The user can fit the strap around the upper body under the pretension which he desires, breathe out and press the button 16, after which the zero adjustment unit sets the LED bar 13 to zero. The variation in the circumference of the upper body, and thus of the depth of the respiration, can then be read off on the LED bar 13. The device described is particularly suitable for training so-called midriff respiration.

Without using the zero adjustment unit 15, it is possible, as an alternative, to provide a detachable coupling between the cord 4 and the detector 6 and to connect the cord 4 to the detector 6 after fitting the strap 1 around the upper body of the user, after the LED bar has been set to zero by manually adjusting the slide 8.

Figure 5:
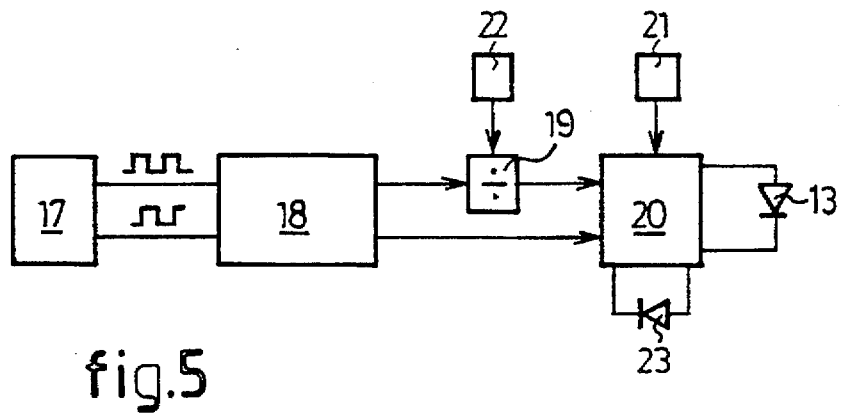
FIG. 5 is an alternative for the processing circuit with display device of the device according to the invention.

An alternative processing circuit is shown in FIG. 5, which circuit is designed with an optical transformer 17, which is designed in a manner known per se with two LED/photodiode pairs, which supply the mutually phase-shifted pulse signals, indicated schematically, if an element constructed with grooves moves relative to the LED/photodiode pairs. Transformers of this type are known per se and do not need to be described here in more detail. These phase-shifted pulse signals are supplied to a detection unit 18, which is likewise designed in a manner known per se and supplies a pulse signal at one output and a direction signal at the other output. The pulse signal is fed via a divider stage 19 to the count input of a counter 20 and the direction signal is fed directly to the up/down input of this counter 20. The counter 20 again controls a LED bar, indicated schematically by an LED 13. The adjustment of the LED bar 13 to zero is particularly simple in the case of the circuit from FIG. 5 and is effected by means of a pushbutton 21, which is connected to the reset input of the counter 20. The sensitivity of the circuit is adjusted by adjusting the division number of the divider stage 19 with the aid of a pushbutton 22.

If desired, both circuits can be fitted with a signalling device which indicates to the user if the input signal from the control stage 12 or the counter 20 falls outside the display range of the LED bar 13. In the case of the circuit according to FIG. 5 it is possible, for example, for the maximum position of the counter 20 to actuate a LED 23 for this purpose. In the case of the embodiment according to FIG. 3, the overflow output of the control stage 12 and the output of the comparator 11 can, for example, be connected to a detection unit 24 which actuates an LED 25 if an overflow signal is received from the control stage 12 or if the output from the comparator 11 indicates that the input signal is smaller than the reference voltage $V_{ref}$.

It will be clear that the circuits shown in FIGS. 3 and 5 serve solely as examples and can be designed in various other ways.

FIG. 6 shows a cross-section like in FIG. 2 of a further embodiment of the strap 1. In the embodiment shown in FIG. 6 two elastic strips 25 have been inserted between the elastic strip of looped strap 2 and the elastic strip of hooked strap 3. The thickness of the strips 25 is at least about equal to the diameter of the cord 4. Thereby a channel 26 for the cord 4 is formed in the strap 1. the cord 4 is taken up in the channel 26 while freely moveable in the longitudinal direction of the strap 1. Any friction between the cord 4 and the looped strap 2 and the hooked strap 3 respectively thereby has been reduced to a minimum.

FIG. 7 shows a variant of the embodiment according to FIG. 6 in which the elastic strips 25 are part of the looped strap 2. Equally well in a corresponding way the elastic strips 25 can be part of the hooked strap 3.

It can be seen from the above that the invention provides a device in which the strap 1 can be fitted around the upper body of the user under a desired pre-tension, so that the user can select a pre-tension which is suitable for him for training the respiration, in particular the midriff respiration. The detector, which is composed of a cord of non-stretchable material and a transformer, functions entirely separately from the strap, the processing circuit comprising adjustment means which can be operated manually and with which the display device can be set to zero in a simple manner, as a result of which the device is very user-friendly. The adjustment of the ratio between measurement signal variation/display range makes it possible to adjust this ratio independently of the degree to which the user has been trained and the like.

The invention is not restricted to the illustrative embodiments described above, which can be varied within the framework of the claims in various ways.

I claim:

1. An assembly for measuring respiration, which comprises:

a.) a strap member of elastic material having means for connecting a free end portion to a position remote thereof for fitting said strap under tension about a body to be measured for respiration;

b.) an elongated member of non-stretchable material extending along said strap member and connected proximate said free end portion;

c.) detector means connected to said elongated member for providing a measurement signal of variation in circumferential length;

d.) circuit means for processing said measurement signal and including an adjusting device; and e.) display means for displaying results of said processed signal, said circuit including means for adjusting display range of said display means.

2. The assembly for measuring respiration as defined in claim 1 wherein said circuit means includes means for resetting to zero said display means.

3. The assembly for measuring respiration as defined in claim 1 wherein said circuit means activates a signaling device if said signal variation is outside a range of said display means.

4. The assembly for measuring respiration as defined in claim 12 wherein said circuit means activates a signaling device of said signal variation is outside a range of said display means.

5. The assembly for measuring respiration as defined in claim 1 wherein said elongated member is disposed within said strap member.

6. The assembly for measuring respiration as defined in claim 1 wherein said strap member is comprised of an elastic strip of loop members and an elastic strip of both members mounted to one another.

7. The assembly for measuring respiration as defined in claim 6 wherein two elastic strips of like material are mounted between said elastic strip of loop members and said elastic strip of both members defining a channel for said elongated member.

* * * * *